US005733784A

United States Patent [19]

Studholme et al.

[11] Patent Number: 5,733,784
[45] Date of Patent: Mar. 31, 1998

[54] REAGENT SYSTEM AND METHOD FOR THE DIFFERENTIATION AND IDENTIFICATION OF RETICULOCYTES

[75] Inventors: Robert M. Studholme, Memphis, Tenn.; Paul N. Marshall, Santa Clara; Anne M. Embleton, Los Gatos, both of Calif.; John G. Glazier, Penbroke Pines, Fla.; Luc Van Hove, San Jose, Calif.

[73] Assignee: Abbott Laboratories, Abbott Park, Ill.

[21] Appl. No.: 560,601

[22] Filed: Nov. 20, 1995

[51] Int. Cl.$^6$ .......................... G01N 33/48; G01N 31/00
[52] U.S. Cl. .............................. 436/63; 436/8; 436/10; 436/17; 436/18; 436/164; 436/166
[58] Field of Search .......................... 436/8, 10, 17, 436/18, 63, 164, 166; 435/2

[56] References Cited

U.S. PATENT DOCUMENTS

| | | | |
|---|---|---|---|
| 4,412,004 | 10/1983 | Ornstein et al. | 436/10 |
| 4,575,490 | 3/1986 | Ornstein et al. | 436/63 |
| 5,045,472 | 9/1991 | Ornstein et al. | 436/10 |
| 5,284,771 | 2/1994 | Fan et al. | 436/10 |
| 5,350,695 | 9/1994 | Colella et al. | 436/63 |
| 5,360,739 | 11/1994 | Fan et al. | 436/63 |
| 5,411,891 | 5/1995 | Fan et al. | 436/63 |
| 5,438,003 | 8/1995 | Colella et al. | 436/63 |
| 5,492,833 | 2/1996 | Rodriguez et al. | 436/63 |

FOREIGN PATENT DOCUMENTS 9427146  11/1994  WIPO.

OTHER PUBLICATIONS

Reticulocyte Counting by Flow Cytometry Proposed Guideline NCCLS Document H44–P vol. 13 No. 18 Nov. 1993.

*Primary Examiner*—Maureen M. Wallenhorst
*Attorney, Agent, or Firm*—Nicholas A. Poulos; Dianne Casuto

[57] ABSTRACT

Whole blood is mixed with a reticulocyte reagent system that has a reticulocyte staining reagent and a diluent reagent, used in combination. This mixture is incubated at room temperature for between about 15 minutes to about 4 hours. The incubated mixture is then analyzed and the light scattering properties of the cells are detected, collected, differentiated and quantitized. Data gathering includes, at least, 10 and 90 degree light scatter detection.

10 Claims, 5 Drawing Sheets

REAGENT SYSTEM AND METHOD FOR THE DIFFERENTIATION AND IDENTIFICATION OF RETICULOCYTES

BACKGROUND

This invention relates to particle analysis in an automated hematology analyzer. In particular this invention relates to a reagent system and method for the detection and identification of reticulocytes in a whole blood sample.

The reticulocyte is an immature red blood cell ("RBC") which still contains reticular material (ribosomal and messenger RNA) even though at this stage of its development the cell has expelled the nucleus. Red blood cells normally enter the blood stream as reticulocytes. Erythropoiesis begins with the erythroblast and proceeds through several generations of intermediate, nucleated cells in the bone marrow, ending with the reticulocyte. Under anemic or hypoxic conditions this process may be shortened, with reticulocytes of an earlier stage than normal entering the blood stream. These early reticulocytes are recognized by the extra quantity of RNA they contain, as well as their larger size, lower content of hemoglobin, and by the greater length of time they persist as reticulocytes in the blood stream.

The reticulocyte count, therefore, relates to red blood cell production and is useful in the diagnosis and treatment of anemia. Reticulocyte counts historically have been very closely associated with the etiology and classification of the anemias. The reticulocyte count is increased in hemolytic anemias, pyruvate kinase deficiency, sickle cell anemia, thalassemias, and decreased in megaloblastic anemia, aplastic anemia, and general bone marrow dysfunction. The reticulocyte count has been used recently to assess the toxic effects of chemotherapeutic agents on the marrow. In short, hematologists unanimously promote the reticulocyte count as an index of RBC production.

The most commonly used method for counting reticulocytes is the manual microscopic procedure. Brilliant Cresyl Blue was predominantly used until New Methylene Blue ("NMB") was introduced in 1949 by Brecher. The most recent National Committee for Clinical Laboratory Standards ("NCCLS") publication (NCCLS document H44-P) calls for the use of a NMB stain in its reference method. An equal volume of blood is mixed with the NMB stain and incubated for at least three minutes, and up to about fifteen minutes to allow the RNA to precipitate. A blood smear is made, and the stained reticulocytes are counted microscopically. A Miller ocular disc is inserted into the eyepiece. The area of the smaller square viewed within the eyepiece is ⅑ that of the larger square. The red blood cells are enumerated in the smaller square, while the reticulocytes are enumerated in the larger square. Twenty successive fields are counted and the proportion of reticulocytes is calculated by dividing total reticulocytes in large squares by total red blood cells in small squares after multiplying by 9, and then multiplying the result by 100. The drawback of the manual method is that it is labor intensive, imprecise, time-consuming and subjective.

Many attempts have been made to correct the shortcomings of the manual method by means of flow cytometric technology using fluorescent dyes. In the 1980's Pyronin Y ("PY") and Acridine Orange ("AO") were used to stain and count reticulocytes on flow cytometers. Several semi-automated, flow cytometric methods are now available to enumerate reticulocytes from a whole blood sample. In each of the existing methods, a diluent containing a cationic dye, such as Auramine O ("AuO"), or Thiazole Orange ("TO") is used to stain the RNA within the reticulocytes. During the incubation period, the dye slowly penetrates the cell membrane and binds to the RNA within each reticulocyte. The amount of signal generated by the stained reticulocytes as the sample passes through the detection zone is proportional to the RNA content within each reticulocyte. A flow cytometer equipped with the proper excitation light source and emission detection system can, therefore, be used to determine the percentage of reticulocytes in a whole blood sample.

A distinguishing feature of these flow cytometric techniques is the use of at least one fluorescent dye. Fluorescence is characterized by the emission of light at a wavelength different from the excitation light. Light at a particular wavelength band is absorbed by the fluorescent material (the fluorophore), and light of a longer band is emitted. The amount of emitted light is significantly smaller than the level of the excitation light. It is necessary to incorporate optical components such as filters to allow the detection and measurement of only the desired fluorescence signal. In contrast, a detection system that detects and measures scattering does not require such filters, since scattered light is of the same wavelength as the incident light. Additionally, lower cost and less powerful light sources can be utilized in non-fluorescence detecting systems since such fluorescence stimulating light sources are not necessary in electro-optical systems based on detecting the light scattering properties of the cells.

U.S. Pat. Nos. 5,350,695 and 5,438,003 to Colella, et al., and 5,284,771 to Fan et al. disclose methods and reagent compositions which comprise treating a whole blood sample with a single reagent solution comprising a cationic dye such as NMB or Oxazine 750 to precipitate and stain RNA in reticulocytes, and a zwitterionic agent to make the cells spherical. Miles inc., an assignee of these patents has recently incorporated some of the above methods into their latest H*3® hematology instrument. This instrument is equipped with a helium/neon ("HeNe") light source, and the dye Oxazine 750 is used to stain and precipitate the RNA within reticulocytes, while a zwitterionic surfactant is used to make the RBCs and reticulocytes spherical in preparation for volumetric measurements. The sensitivity of the method in detecting Group IV reticulocytes has proven to be poor.

A different approach is taken by the Coulter Corporation in WO 94/27146. Here a NHB stained sample is manually treated with a sulfuric acid based reagent to "ghost" the RBCs. Coulter calls its technology VCS (Volume, Conductivity and Scatter) and has incorporated such a semi-automated reticulocyte method onto their STKS® and MAXM™ hematology analyzers. In the Coulter VCS reticulocyte determination, the blood specimen is mixed off-line with NMB stain and incubated at room temperature for 5 minutes. A small volume of the stained blood sample is then diluted with a clearing solution which contains sulfuric acid. The clearing or "ghosting" solution causes the cell to swell, becoming spherical, and the hemoglobin to leak out of the cell. The prepared sample, after a prescribed and very critical time period, is then aspirated into a Coulter STKS® or MAXM™ hematology analyzer to complete the analysis. Reticulocytes, mature RBCs, leukocytes and platelets are discriminated on the basis of a combination of light scatter, and impedance (volume) measurements. However, timing is extremely critical for the ghosting stage: too long a time will cause the lysis of the RBCs; too short will result in poor resolution of reticulocytes and mature RBCs.

Both the Miles, Inc. and the Coulter procedures therefore present significant problems and require effort on the part of the instrument operator to assure accurate determinations. This is especially the case with regard to staining time and "ghosting" the stained preparation.

Accordingly there is a need for a reticulocyte process that can be adapted to existing hematology analyzers without significant hardware changes or requiring the substitution, or change over, of on-board reagents.

SUMMARY OF THE INVENTION

Reagents and method for the differentiation and concentration determination of reticulocytes in a blood sample are provided.

In particular, a reagent system that comprises a reticulocyte staining reagent and a diluent reagent are provided to enable automated, light scatter determinations of reticulocytes.

More particularly, the reagent system of this invention is utilized to stain and protect reticulocytes in the hypotonic (lytic) environment of an automated electro-optical hematology analyzer.

Generally, the reticulocyte staining reagent component of the reagent system comprises a nonionic or zwitterionic agent to make the RBCs spherical, an over abundance of dye which stains and precipitates any nucleic acid material within RBCs and a high concentration of an electrolyte.

Preferably, the reticulocyte staining reagent comprises from about 0.7 to about 1.3 grams of a nucleic acid dye per liter of diluent reagent, wherein the dye is selected from the group consisting of Azure B, New Hethylene Blue, Brilliant Cresyl Blue and Oxazine 750, from about 3 to about 7 milligrams of a reticulocyte sphering agent per liter of diluent reagent selected from the group consisting of n-dodecyl β-D maltoside, N-dodecyl-N, N-dimethyl-3-ammonio-1-propanesulfonate (DDAPS) and N-tetradecyl-N, N-dimethyl-3-ammonio-1-propanesulfonate (TDAPS), and from about 17 to about 23 grams per liter of diluent reagent of an electrolyte selected from the group consisting of the ammonium, potassium and sodium salts of oxalic acid.

Hose preferably the reticulocyte staining reagent comprises from about 19.0 to about 21.0 grams of potassium oxalate, monohydrate; from about 0.95 to about 1.05 gram of New Methylene Blue; from about 4.75 to about 5.25 mg of n-dodecyl β-D-maltoside; and about 1.0 liter of the diluent reagent.

The diluent reagent component of the reagent system, used separately or in combination with the formulation of the reticulocyte staining reagent, comprises from about 2.33 to about 2.57 gram sodium phosphate, dibasic; from about 0.38 to about 0.42 gram potassium phosphate, monobasic; from about 0.18 to about 0.22 gram disodium EDTA, dihydrate; from about 7.25 to about 8.86 sodium chloride; from about 0.36 to about 0.44 gram potassium chloride; from about 0.28 to about 0.35 gram Proclin 300; and deionized water, to 1 liter.

More preferably the diluent reagent comprises from about 2.33 to about 2.57 grams sodium phosphate, dibasic; from about 0.38 to about 0.42 gram potassium phosphate, monobasic; from about 0.19 to about 0.21 gram disodium EDTA, dihydrate; from about 7.65 to about 8.45 grams sodium chloride; from about 0.38 to about 0.42 gram potassium chloride; from about 0.30 to about 0.33 gram Proclin® 300 (5-chloro-2-methyl-4-isothiazolin-3-one (2.0–2.5%) and 2-methyl-4-isothiazolin-3-one (0.7–0.9%); and deionized water to 1 liter. The pH of diluent reagent is in the range of about 7.2 to about 7.6, with an osmolarity of greater than 550 mOs/kg.

Another aspect of the invention provides for a method for differentiating and quantifying reticulocytes in a blood sample. The method comprises the combining of from about 3.7 to about 4.3 ml of the above reticulocyte staining solution with from about 10 µl to about 40 µl of anticoagulated whole blood. The resulting mixture is incubated from about 15 minutes to about 4 hours. Then the mixture is passed, substantially one cell at a time through an illuminated flow cell and at least 10° and 90° light scatter data from the illuminated flow stream is collected. The collected data is then analyzed and reticulocytes are differentiated therefrom.

DETAILED DESCRIPTION OF PREFERRED EMBODIMENTS

Embodiments of the invention generally comprise reagents for, and methods of, quantifying the concentration of reticulocytes in a sample of blood. More particularly the method and reagents combine to stain and detect reticulocytes in a blood sample. The stained sample can then be analyzed by an automated hematology analyzer. Light scatter data is collected with the reticulocyte content of the sample being quantified.

In general, the method comprises the incubation of a blood sample with one or more reagents. The stained sample is then analyzed on an automated electro-optical hematology analyzer such as the Cell-Dyn® 3500 hematology instrument, available from Abbott Laboratories' Diagnostics Division, Santa Clara, Calif. This type of instrument analyzes a sample of anticoagulated blood, performing one or more optical and electrical measurements, yielding quantitative hematological information concerning the blood sample.

In a preferred embodiment, a CELL-DYN® 3500 hematology instrument is modified to facilitate the quantification of the reticulocytes. Modifications are effected in the software which controls the operation of the instrument. Examples of such software modifications are illustrated in the flow scripts of FIG. 5. The modified analysis procedure is generally similar to the white blood cell optical analysis (WOC) performed by that instrument in an unmodified form, with at least 0°, 10° and 90° light scatter data utilized. The principal modifications comprise the elimination of an incubation of the blood sample that normally occurs with the instrument's on-board hypotonic sheath reagent; the disablement of the optical blood sensor; and the implementation of a new data acquisition and analysis program.

In one embodiment, a reagent system is provided. One component of this system is a reticulocyte staining reagent that comprises from about 0.7 to about 1.3 grams of a nucleic acid dye selected from the group consisting of Azure B, New Methylene Blue ("NMB"), Brilliant Cresyl Blue and Oxazine 750, from about 3 to about 7 milligrams of a reticulocyte sphering agent selected from the group consisting of n-dodecyl β-D-maltoside, N-dodecyl-N, N-dimethyl-3-ammonio-1-propanesulfonate (DDAPS) and N-tetradecyl-N, N-dimethyl-3-ammonio-1-propanesulfonate (TDAPS), from about 17 to about 23 grams of an electrolyte selected from the group consisting of the ammonium, potassium and sodium salts of oxalic acid. This staining reagent is combined prior to or during use with a diluent reagent. The concentrations listed above and hereafter are based upon a per liter concentration with the diluent reagent.

The diluent reagent component of the reagent system, used in combination with the reticulocyte staining reagent, comprises from about 2.33 to about 2.57 gram sodium phosphate, dibasic; from about 0.38 to about 0.42 gram potassium phosphate, monobasic; from about 0.18 to about 0.22 gram disodium EDTA, dihydrate; from about 7.25 to about 8.86 gram sodium chloride; from about 0.36 to about 0.44 gram potassium chloride; from about 0.28 to about 0.35 gram Proclin® 300; and deionized water, to 1 liter.

The present method comprises, in one embodiment, adding about 20 μl of whole blood, mixed with EDTA to prevent coagulation, to about 4 ml of the reticulocyte reagent system described above and incubating this mixture at room temperature for between about 15 minutes to about 4 hours. The incubated mixture is then presented to an analytical instrument where the light scattering properties of the cells are detected, collected, differentiated and quantified. Data gathering includes, at least, 10 and 90 degree light scatter measurements. 0 degree scatter signals may also be utilized, especially for use as a threshold for the 10 and 90 degree scatter signals.

Figure 5:
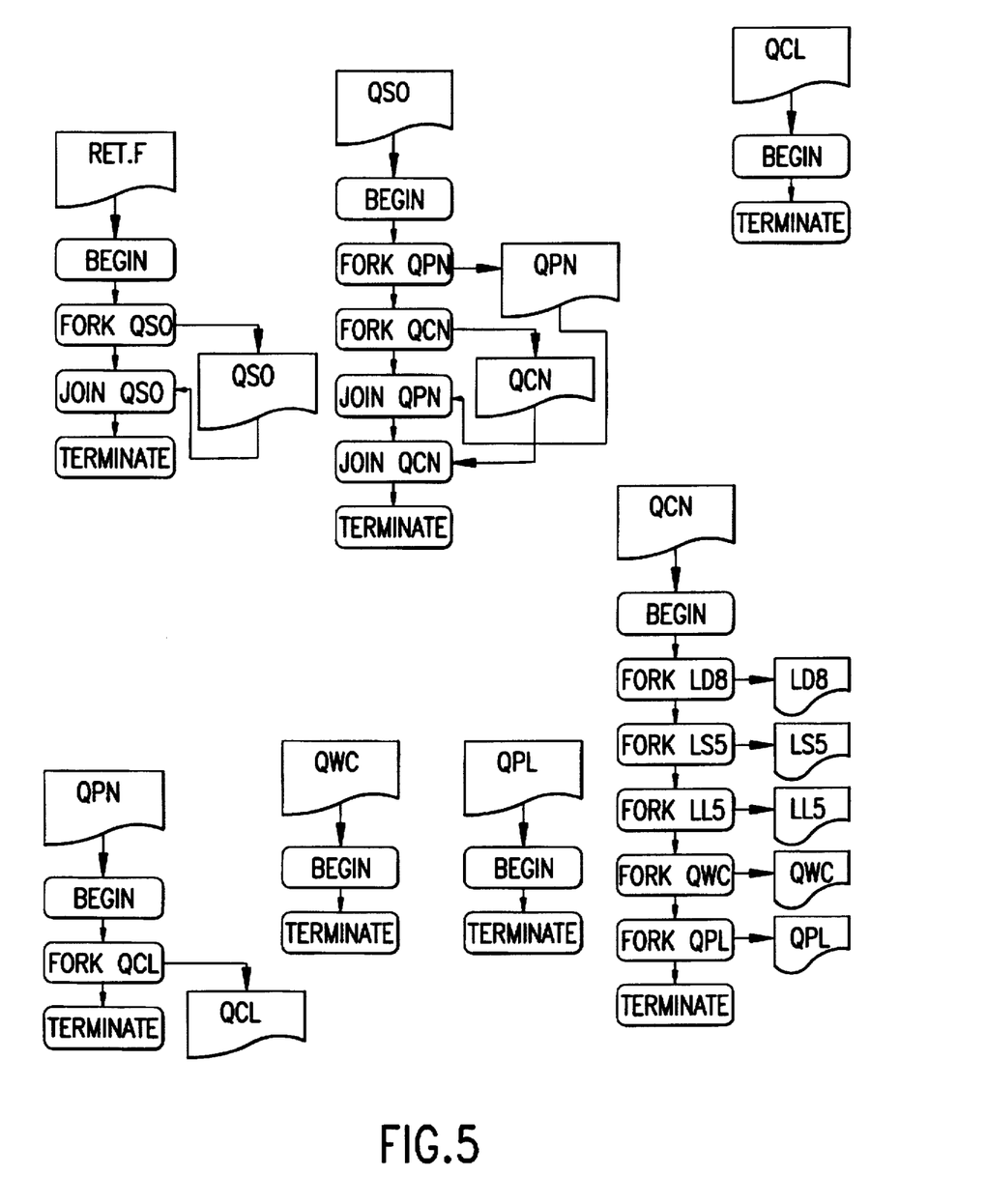
FIG. 5 is a flow chart of the software flow scripts for the modification to a commercial hematology analyzer.

The following illustrative description of an embodiment of the analysis procedure refers to the components, processes, and data outputs of a CELL-DYN® 3500 as modified by the flowscript software exemplified in FIG. 5. It is anticipated that such a modified CELL-DYN® 3500 instrument will be commercially available from Abbott Laboratories, assignee in interest of this invention, sometime in 1996.

An important advantage of the reagent system and method of this invention is the protection the reagents, particularly the diluent component, confers upon the reticulocytes when they are subjected to the hostile environment of an analyzer that utilizes a lyric sheath reagent. This advantage means that costly instrument hardware modifications and on board reagents, or reagent changeovers are not necessary.

Once modified, the software routine, or flowscript ("RET"), illustrated in FIG. 5, is implemented by selecting the "RETIC" option from the "SPECIMEN TYPE" menu presented to the operator of the CELL-DYN® 3500. When analyzing for reticulocytes, other routine analyses such as RBC measurement, WBC impedance measurements, or hemoglobin measurements are not executed.

When the touch plate is pressed, flowscript RET is initiated. Flowscript RET calls upon sequence QSO (see Appendix), waits for sequence OSO to terminate, and then terminates.

Sequence QSO causes a sample of blood (incubated with the reagent as described above) to be aspirated into the open probe for about 3.3 seconds. The blood sample sensor of the CELL-DYN® 3500 is not utilized in this modified flowscript due to the previous dilution of the sample during its pretreatment process. The aspirated portion of the sample is then transferred to the shear valve by a peristaltic pump, and the open probe cleaning block moves to enable cleaning of the open probe. This routine then begins sequences QPN and QCN, waits for them to terminate, and then terminates.

Sequence QCN, one of the sequences called by QSO, prepares the WOC mixing chamber to receive the sample from the shear valve. This routine fills the diluent reservoir via sequence LD8 (not modified from the standard version used with the CELL-DYN® 3500). The sample and reagent are transferred to the WOC mixing chamber by a syringe pump, and sequence LS5 (not modified from the standard version used with the CELL-DYN® 3500) fills the sheath reservoir with the standard Cell-Dyn® 3500 sheath reagent. The waste chambers are emptied, the samples are mixed, and sequence QWC is called to begin the WOC (optical counting) measurements. Data buffers are cleared before data from the optical measurements are collected. The routine then rotates the shear valve to the aspirate position. The CELL-DYN® 3500 data station is instructed to receive data from the optical measurements, and sequence QPL is called to clean the flow panel. QCN then terminates. Sequence QPN, the other routine called upon by QSO, aspirates excess blood from the open sample aspiration probe and the closed sample aspiration probe (not used in the reticulocyte analysis, but aspirated to clear the Y fitting) and cleans the open sample aspiration line. The outside of the open sample aspiration probe is cleaned, and sequence QCL is called. Sequence QPN then terminates.

Sequence QWC is called by sequence QCN. It transfers the sample to the WOC sample passage, pressurizes this passage to about 9 psi, and injects the sample into the WOC flow cell. Diluent reagent flow (as formulated above) is initiated through the WOC flow cell, and a 9 psi accumulator inlet is shut to ensure the sheath flow is routed through the flow cell. Data gathering is performed by collecting 10 degree and 90 degree scatter signal as described in the following examples. 0° scatter is utilized to trigger the 10° and 90° data collection. When the optical data collection is completed, sequence OWC terminates.

Sequence QPL is called by sequence QCN. This routine recharges the secondary 12 inch of mercury vacuum accumulator, empties waste chamber #2, fills the WOC sample syringe, and cleans the WOC sample passage. The pressure in the reagent lines to the shear valve is relieved, the sample mix lines are cleared, and the list mode data collection is turned off, after which sequence QPL terminates.

Specific data analysis methods are described in the following examples.

EXAMPLE 1

Quantification of Reticulocytes in a Whole Blood Sample

1. A reagent solution was prepared by mixing about 20.0 grams of potassium oxalate, monohydrate, about 1.0 gram of New Hethylene Blue, and about 5.0 mg of n-dodecyl β-D-maltoside (all available from Sigma Chemical Company, St. Louis, Mo.) with about 1.0 liter of a diluent reagent. The composition of the diluent reagent was: sodium phosphate, dibasic, 2.45 grams; potassium phosphate, monobasic, 0.40 gram, disodium EDTA, dihydrate 0.20 gram, sodium chloride 8.05 grams; potassium chloride, 0.40 gram; Proclin® 300 0.315 gram; and deionized water, to 1 liter. The pH of diluent reagent was in the range of from about 7.2 to about 7.6 and its osmolarity >550 mOs/kg.

2. About 20 μl of whole blood, mixed with EDTA to prevent coagulation, was then mixed with about 4 ml of the reagent solution and incubated at room temperature from about 15 minutes to 4 hours.

3. The sample was aspirated into and analyzed by a Cell-Dyn® 3500 hematology analyzer in the WOC channel utilizing the standard Cell-Dyn® 3500 reagents normally utilized for the WBC analysis. The flowscript of the analyzer was modified to eliminate the usual incubation of the blood and the sheath reagent, and to disable the infrared sensor that would normally detect the aspiration of the blood sample. Both of these modifications are accomplished by the flowscripts disclosed in FIG. 5.

4. Data consisting of at least the 10 degree scatter and 90 degree scatter values for up to 30,000 events are acquired and stored by the instrument. The data are stored as 8-bit numbers ranging from 0 to 255.

5. Data for events with off scale values, such as 10 degree scatter values of 255 or 90 degree scatter values of 255, are removed from the analysis.

6. Data for events associated with platelet clumps and coincident events are removed as follows:
   a. The standard deviation of the remaining 10 degree scatter data is calculated. An exemplary histogram of 10 degree scatter values for a patient sample following removal of off scale values is presented in FIG. 1.
   b. The mode of the remaining 10 degree scatter data is determined using the procedure described in Example 2.
   c. Data for all events whose 10 degree scatter values are more than about two standard deviations higher or lower than the calculated mode are removed from the analysis.

7. The reticulocytes are quantified from the remaining data as follows:
   a. The mode for the remaining 90 degree scatter data is calculated using the procedure described in Example 2. A histogram of the 90 degree scatter data for the same sample as in FIG. 1 (following removal of platelet clumps and coincident events) is illustrated in FIG. 2.
   b. All events with 90 degree scatter values that are greater than two approximately times the 90 degree scatter mode are considered reticulocytes.
   c. The reticulocyte count is adjusted by subtracting a value equal to 0.002 times the total number of events measured by the instrument (the so-called instrument "raw count"), yielding the adjusted reticulocyte count.
   d. The reticulocyte percentage is calculated by dividing the adjusted reticulocyte count by the number of remaining 10° scatter events (the events remaining in the analysis following the completion of step 6).

Figure 1:
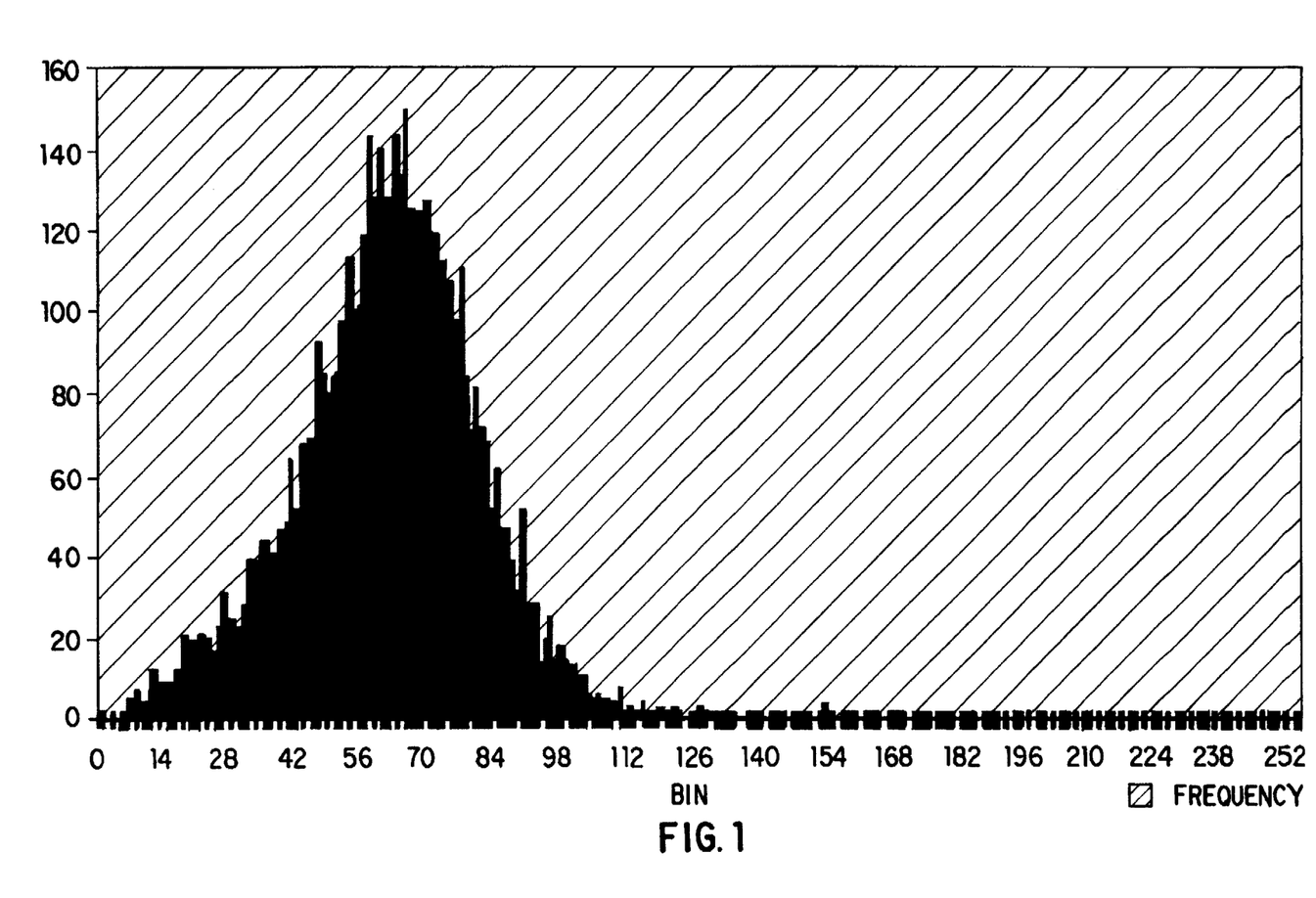
FIG. 1 is an exemplary histogram of 10 degree scatter values for a patient sample following removal of off scale values as described in Example 1.
Figure 2:
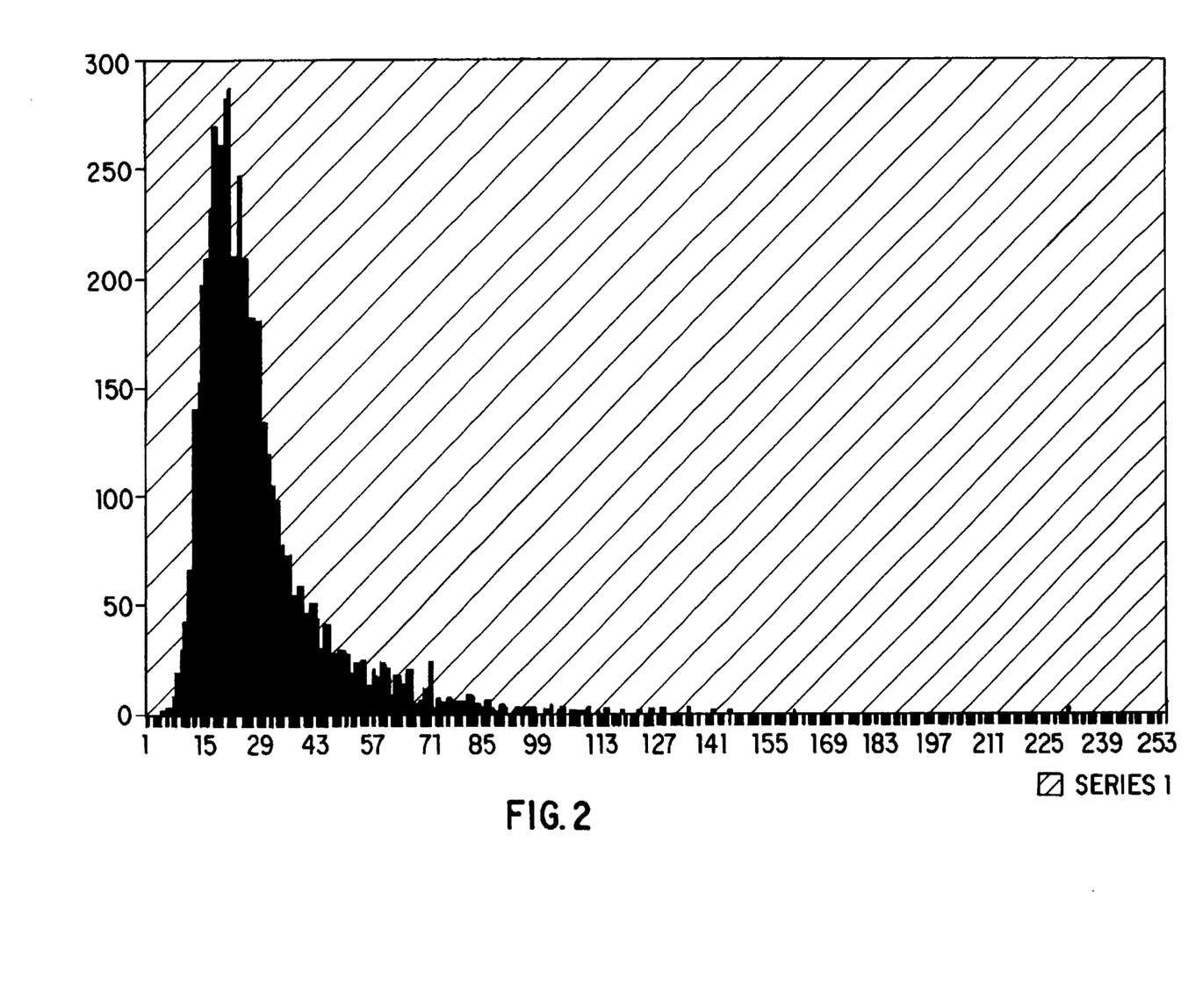
FIG. 2 is an illustration of a histogram of the 90 degree scatter data for the same sample as in FIG. 1, following removal of patient clumps and coincident events as described in Example 2.
Figure 3:
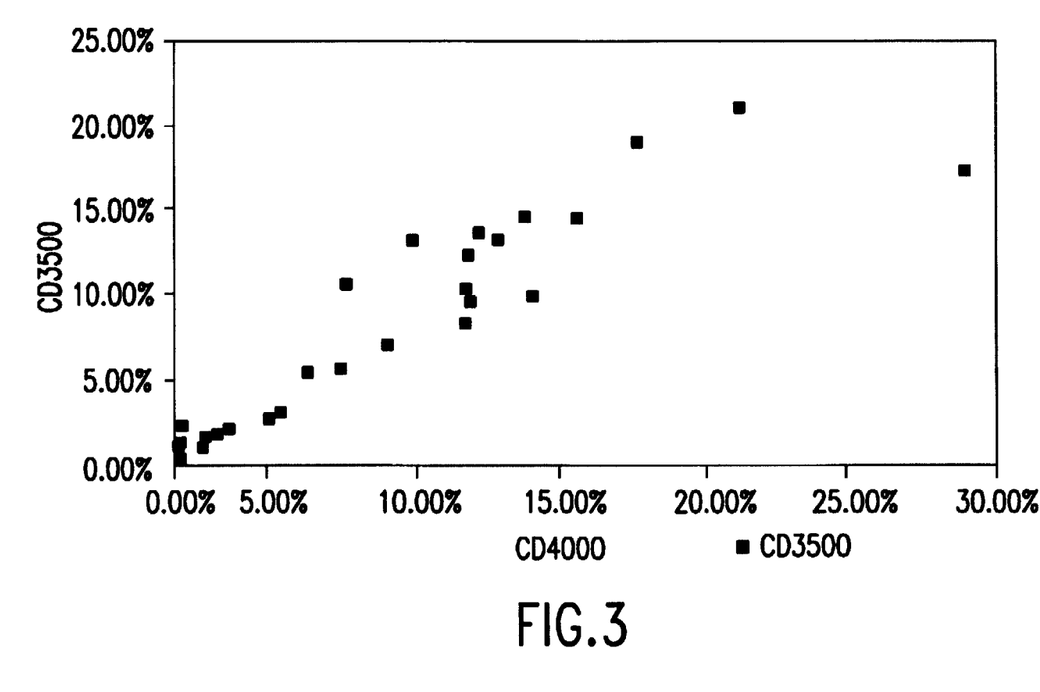
FIG. 3 shows the correlation of the results of the current reticulocyte assay with another reference method.
Figure 4:
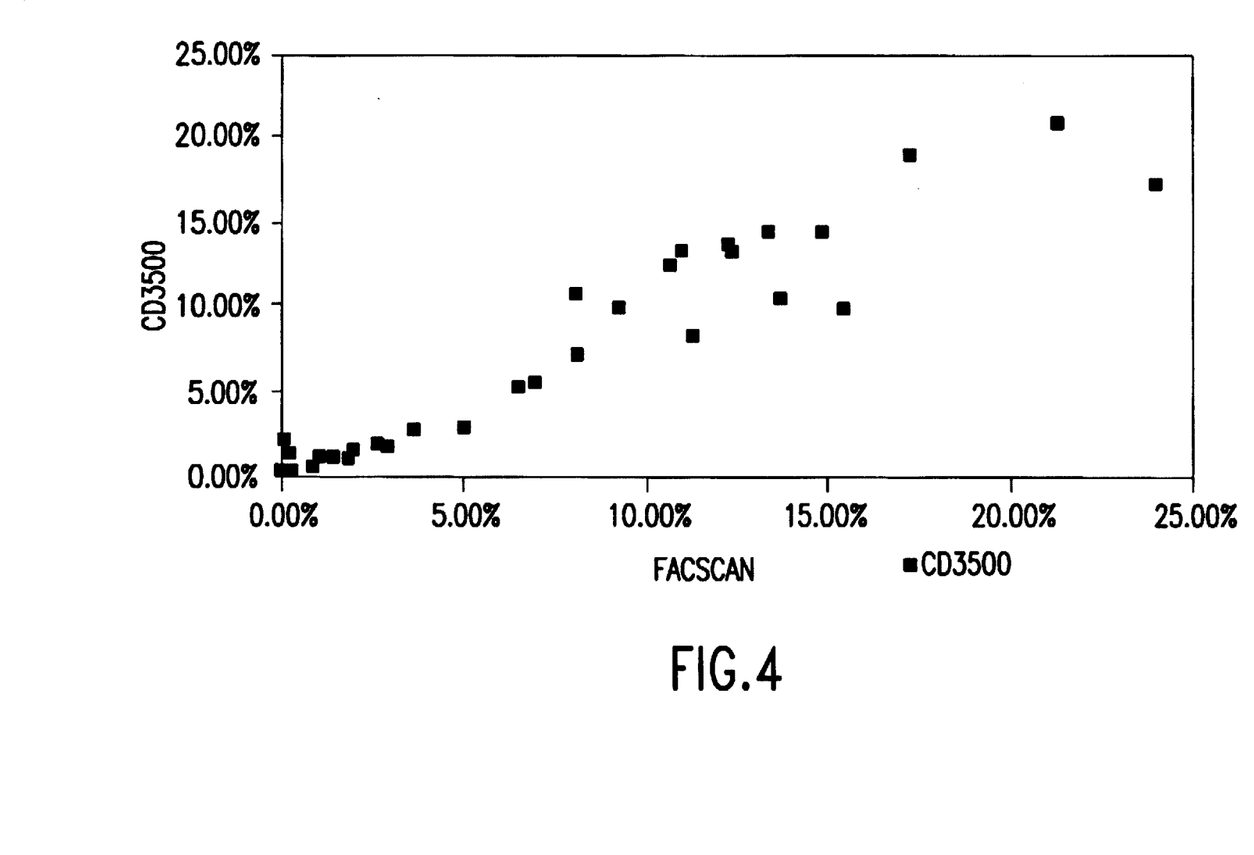
FIG. 4 shows the correlation of the results of the current reticulocyte assay with another reference method.

In the example illustrated in FIGS. 1 and 2, the reticulocyte percentage was 13.25 percent. Linear regression and correlation analyses of the current reticulocyte assay and reference procedures are shown in FIGS. 3 and 4. FIG. 3 portrays the reticulocyte fraction determined by this method (labeled "CD3500") versus the reticulocyte fraction determined by an independent method (labeled "CD4000") for blood samples from 38 patients. The independent method is described in detail in U.S. patent application Ser. No. 08/426,408, filed Apr. 21, 1995 and entitled COMPOSITIONS AND METHODS FOR THE RAPID ANALYSIS OF RETICULOCYTES. The correlation coefficient between the two methods is 0.937, indicating the accuracy of the method described here. The slope of the best fitting straight line is 0.85, with a y-intercept of 0.95. FIG. 4 portrays the reticulocyte fraction determined by this method (labeled "CD3500") versus the reticulocyte fraction determined using the FACScan® instrument/thiazol orange reagent system, available from Becton Dickinson and Company, San Jose, Calif. (labeled "Facscan"), for the same 38 blood samples. The correlation between these two methods is 0.959, with a slope of 0.91 and y-intercept of 0.1 for the best fitting straight line, further indicating the accuracy and demonstrating the usefulness of this method of analysis.

EXAMPLE 2

Calculation of Scatter Data Modes

The calculation of the mode of scatter values as described in Example 1, may be performed as follows:

1. A 256 bin histogram is created for the values of scatter data whose mode is desired.

2. The histogram is smoothed four (4) times by applying the binomial smoothing algorithm:

$$M_i = 0.1N_{i-2} + 0.2N_{i-1} + 0.4N_i + 0.2N_{i+1} + 0.1N_{i+2}$$

where $N_i$ is the initial contents of bin i, and $M_i$ is the smoothed contents of bin i.

3. The maximum value of the four-times smoothed histogram is divided by two (2) to yield the 50% value.

4. The bin in the original (unsmoothed) histogram which is the highest bin below the peak whose contents number less than or equal to the 50% value is termed the low channel. The number of data points in this bin and all bins below this bin are termed the low channel points.

5. The bin in the original (unsmoothed) histogram which is the lowest bin above the peak whose contents number less than or equal to the 50% value is termed the high channel. The number of data points in this bin and all bins below this bin are termed the high channel points.

6. The point is located which bisects the number of points between the high and low channel:
   a. The low channel points are subtracted from the high channel points, yielding the difference.
   b. Half (0.5) of the difference is added to the low channel points, yielding the number of events in and below the midpoint channel (the midpoint channel value).
   c. The lowest channel for which the number of data points in and below that channel is equal to or greater than the midpoint channel value is located.

7. The channel located in step 6 is termed the mode and used for further analysis as described in Example 1.

EXAMPLE 3

Quantification of Reticulocytes

In an alternative embodiment:

1. Steps 1 through 5 of Example 1 are performed, yielding data including 10 and 90 degree scatter values for up to 30,000 cellular events.

2. The data from step one is divided into about 4 to 6 substantially equally sized groups (from about 5,000 to 7,500 events each).

3. The analysis procedures of step 6 through step 7b of Example 1 are performed independently for each group, yielding 4 to 6 values of group reticulocyte counts which are summed to yield the reticulocyte count.

4. The reticulocyte count is adjusted by subtracting 0.002 times the total number of events detected by the instrument (the so-called instrument "raw count").

5. The reticulocyte fraction is calculated by dividing the adjusted reticulocyte count by the sum of the events in each group remaining after the removal of off-scale events, platelet clumps, and coincident events as described in Example 1.

We claim:

1. A reagent system for the determination of reticulocytes comprising:
   (1) a diluent reagent which comprises:
      a. from about 2.33 to about 2.57 gram sodium phosphate, dibasic,
      b. from about 0.38 to about 0.42 gram potassium phosphate, monobasic,
      c. from about 0.18 to about 0.22 gram disodium EDTA, dihydrate,
      d. from about 7.25 to about 8.86 gram sodium chloride,
      e. from about 0.36 to about 0.44 gram potassium chloride,
      f. from about 0.28 to about 0.35 gram 5-chloro-2-methyl-4-isothiazolin-3-one (2.0–2.5%) and 2-methyl-4-isothiazolin-3-one (0.7–0.9%), and
      g. deionized water to 1 liter, the diluent reagent having a pH from about 7.2 to about 7.6, with an osmolarity of greater than 550 mOs/kg
   (2) a reticulocyte staining reagent which comprises:
      a. from about 0.7 to about 1.3 grams of a nucleic acid dye selected from the group consisting of Azure B, New Methylene Blue, Brilliant Cresyl Blue and Oxazine 750,
      b. from about 3 to about 7 milligrams of a reticulocyte sphering agent selected from the group consisting of n-dodecyl β-D-maltoside, N-dodecyl-N,N-dimethyl-3-ammonio-1-propanesulfonate (DDAPS) and N-tetradecyl-N,N-dimethyl-3-ammonio-1-propanesulfonate (TDAPS), and
      c. from about 17 to about 23 grams of an electrolyte selected from the group consisting of ammonium, potassium and sodium salts of oxalic acid, wherein (a), (b) and (c) are per liter of said diluent reagent.

2. The reagent system of claim 1 wherein the reticulocyte staining reagent comprises from about 19.0 to about 21.0 grams of potassium oxalate, monohydrate; from about 0.95 to about 1.05 grams of New Methylene Blue; and about 4.75 to about 5.25 mg of n-dodecyl β-D-maltoside.

3. The reagent system of claim 2 wherein the reticulocyte staining reagent comprises about 20.0 grams of potassium oxalate, monohydrate; about 1.0 gram of New Hethylene Blue; and about 5.0 mg of n-dodecyl β-D-maltoside.

4. The reagent system of claim 1 wherein the diluent reagent comprises from about 2.33 to about 2.57 gram sodium phosphate, dibasic, from about 0.38 to about 0.42 gram potassium phosphate, monobasic, from about 0.19 to about 0.21 gram disodium EDTA, dihydrate, from about 7.65 to about 8.45 gram sodium chloride, from about 0.38 to about 0.42 gram potassium chloride, and from about 0.30 to about 0.33 gram 5-chloro-2-methyl-4-isothiazolin-3-one (2.0–2.5%) and 2-methyl-4-isothiazolin-3-one (0.7–0.9%).

5. The reagent system of claim 4 wherein the diluent reagent comprises about 2.45 grams sodium phosphate, dibasic, about 0.40 gram potassium phosphate, monobasic, about 0.20 gram disodium EDTA, dihydrate, about 8.05 grams sodium chloride, about 0.40 gram potassium chloride, and about 0.315 gram 5-chloro-2-methyl-4-isothiazolin-3-one (2.0–2.5%) and 2-methyl-4-isothiazolin-3-one (0.7–0.9%).

6. A method of differentiating reticulocytes in a whole blood sample comprising:
   a. mixing an aliquot of said blood sample with a reticulocyte reagent system to form a sample/reagent mixture, wherein the reticulocyte reagent system comprises (1) a reticulocyte staining reagent comprising from about 0.7 to about 1.3 grams of a nucleic acid dye selected from the group consisting of Azure B, New Methylene Blue, Brilliant Cresyl Blue and Oxazine 750, from about 3 to about 7 milligrams of a reticulocyte sphering agent selected from the group consisting of n-dodecyl β-D-maltoside, N-dodecyl-N,N-dimethyl-3-ammonio-1-propanesulfonate (DDAPS) and N-tetradecyl-N,N-dimethyl-3-ammonio-1-propanesulfonate (TDAPS), and from about 17 to about 23 grams of an electrolyte selected from the group consisting of ammonium, potassium and sodium salts of oxalic acid; and (2) about 1 L of a diluent reagent having a pH from about 7.2 to about 7.6, with an osmolarity of greater than 550 mOs/kg, wherein the diluent reagent comprises from about 2.33 to about 2.57 gram sodium phosphate, dibasic, from about 0.38 to about 0.42 gram potassium phosphate, monobasic, from about 0.19 to about 0.21 gram disodium EDTA, dihydrate, from about 7.65 to about 8.45 gram sodium chloride, from about 0.38 to about 0.42 gram potassium chloride, and from about 0.30 to about 0.33 gram 5-chloro-2-methyl-4-isothiazolin-3-one (2.0–2.5%) and 2-methyl-4-isothiazolin-3-one (0.7–0.9%);
   b. incubating the sample/reagent mixture from about 15 minutes to about 4 hours;
   c. passing the sample/reagent mixture substantially one cell at a time through an area of focused optical illumination, wherein during such passing the sample/reagent mixture is caused to flow in a stream and the stream is further sheathed within a flowing stream of a hypotonic sheath reagent;
   d. detecting light scattered by cells in the stream and generating data therefrom;
   e. collecting generated scattered light data; and
   f. differentiating reticulocytes from other cells within the stream at least in part upon the basis of the collected scattered light data.

7. The method of claim 6 wherein the scattered light is detected at angles of about 0°, 10°, and 90°.

8. The method of claim 6 wherein the differentiating of reticulocytes is based at least in part on 10° and 90° scattered light.

9. The method of claim 8 wherein platelet clumps and coincident events are eliminated by means of the collected 10° scattered light data.

10. The method of claim 6 wherein from about 3.7 to about 4.3 ml of the reticulocyte reagent system is mixed with from about 10 µl to about 40 µl of anticoagulated whole blood.

* * * * *